Figure 1:
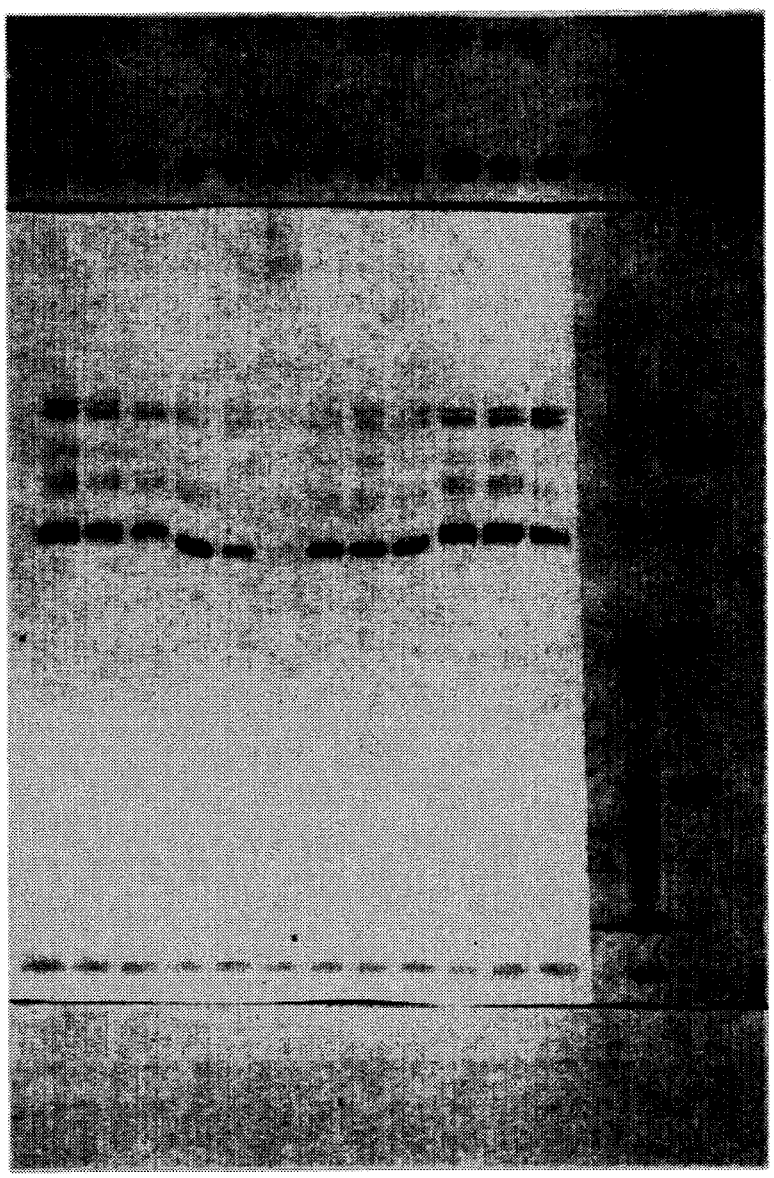

United States Patent [19]

Rasmussen et al.

[11] Patent Number: 5,610,033
[45] Date of Patent: Mar. 11, 1997

[54] METHOD OF PRODUCING PROTEINS WITH FVIII ACTIVITY AND/OR FVIII DERIVATIVES

[75] Inventors: Poul B. Rasmussen, Hellerup; Ole Nordfang, Hillerod, both of Denmark

[73] Assignee: Novo Nordisk A/S, Bagsvaerd, Denmark

[21] Appl. No.: 320,773

[22] Filed: Oct. 11, 1994

Related U.S. Application Data

[63] Continuation of Ser. No. 877,347, Apr. 30, 1992, abandoned, which is a continuation of Ser. No. 514,072, Apr. 25, 1990, abandoned.

[51] Int. Cl.⁶ ............................. C12N 15/00; C12N 5/00; C12P 21/06; C07H 21/04
[52] U.S. Cl. ................... 435/69.1; 435/69.6; 435/320.1; 435/172.3; 530/383; 536/23.5
[58] Field of Search ............................. 435/172.3, 69.1, 435/69.6, 320.1, 240.2; 530/383

[56] References Cited

U.S. PATENT DOCUMENTS

4,746,608  5/1988  Mizukami et al. ..................... 435/68

FOREIGN PATENT DOCUMENTS

0150735  8/1985  European Pat. Off. .
0232112  8/1987  European Pat. Off. .

OTHER PUBLICATIONS

Kaufman et al J.B.C. 263:6352, 1988.
Sebingin. CRC Certified Review Clim. Lab. Sci. 23(1):43, 1986.

*Primary Examiner*—Suzanne E. Ziska
*Attorney, Agent, or Firm*—Steve T. Zelson, Esq.; Cheryl H. Agris, Esq.

[57] ABSTRACT

In a process for producing proteins with FVIII activity and FVIII derivatives by in vitro culturing of mammalian cells, the culturing is carried out at temperatures below 32° C. and the culturing times used are below 24 hours.

3 Claims, 1 Drawing Sheet

METHOD OF PRODUCING PROTEINS WITH FVIII ACTIVITY AND/OR FVIII DERIVATIVES

This application is a continuation application of application Ser. No. 07/877,347, filed Apr. 30, 1992, now abandoned which is a continuation of application Ser. No. 07/514,072, filed Apr. 25, 1990, now abandoned, the contents of which are incorporated herein by reference.

The present invention relates to a method of producing proteins with FVIII activity and/or FVIII derivatives by in vitro culturing of mammalian cells.

The bleeding disorder Hemophilia A is caused by the absence of Factor VIII (FVIII). FVIII is a glycoprotein which can be isolated from blood plasma (U.S. Pat. No. 4,650,858). Purified FVIII is used in the treatment of Hemophilia A. By the use of gene technology it is possible to synthesize FVIII (EPO 160,457, WO 85/01961, U.S. Pat. No. 570,062). The amount of FVIII, which can be produced in mammalian cells is rather low compared with other human proteins. The amount of protein can be increased if truncated variants of FVIII are biosynthesized (WO 86/06101, DK 3442/87), or if the two subunits (FVIII heavy chain and FVIII light chain) are coproduced (U.S. Pat. No. 822,989). It is also possible in vitro to assemble active FVIII from separately produced subunits (DK 2957/86). The above-mentioned forms of FVIII all have the characteristics of human FVIII: activity in bioassays, activable by thrombin, and biological activity in hemophilia dogs.

Mammals are in part characterized by the ability to keep a constant body temperature near 37° C. Therefore mammalian cells in general are grown in vitro at 37° C. FVIII circulates in the body at that temperature, and by culturing in serum containing medium (which mimic body fluid) one may expect that FVIII has optimal stability. FVIII produced in serum free medium is rather unstable, but nevertheless it is attractive to omit serum from the medium, and WO 87/04187 shows that FVIII can be stabilized in serum free medium by addition of the carrier protein von Willebrand Factor (vWF). DK 3594/87 shows that FVIII can also be stabilized in serum free medium by addition of lipoproteins. These stabilizing agents exhibit no pronounced effect in serum containing medium.

It has surprisingly been found that by culturing mammalian cells at a temperature below 37° C., more precisely below 33° C., the yields of truncated FVIII variants and of FVIII derived subunits (especialy FVIII heavy chain) are increased drastically, both in serum containing and in serum free medium.

It is preferred to carry out the culturing at a temperature from 10° to 32° C., more preferred at a temperature from 25° to 30° C., and most preferred at 27° C.

Furthermore it has surprisingly appeared that the yields are raised by shortening the medium residence time below the usual 24–72 hours, which normally gives the optimal yields from mammalian cells.

It is preferred to use a medium residence time of 30 hours or below, more preferred 24 hours or below, even more preferred 10 hours or below, and most preferred below 4 hours.

The combined effect of low growth temperature and short medium residence time is especially pronounced in the case of FVIII heavy chain for which the yield can be raised 25 times.

The increased yield of FVIII heavy chain (HC) at low temperature and short medium residence time can be related to unstability of the product at normal growth conditions. Table 1 shows that FVIII heavy chain at 37° C. loses the ability to combine with FVIII light chain. FIG. 1 shows that FVIII heavy chain form aggregates at 37° C. These aggregates can be dissolved upon reduction. Truncated variants of FVIII may behave like FVIII-HC and form aggregates at high temperature. However, the increased yield at low temperature may also be caused by other factors than a decrease in aggregation. For example a greater resistance against proteolytic degradation might be important.

The preferred host cells will include mammalian cells such as CHO cells, COS-7 monkey cells, melanoma cell lines such as Bowes cells, mouse L-929 cells 3T3 lines, Balb-c or NIH mice, BHK or HAK hamster cell lines and the like.

The examples show that the yields of truncated FVIII variants, FVIII heavy chain, FVIII light chain and FVIII obtained from cells cotransfected with plasmids encoding each of the two subunits are increased at low temperature.

TABLE 1

| Lane | Incubation of FVIII-HC sample | Treatment for SDS-PAGE (FIG. 1) | Combination capacity for diluted sample, FVIII:C mU/ml |
|---|---|---|---|
| 5 | 0 h, 37° C. | reduced | |
| 6 | 4 h, 37° C. | — | |
| 7 | 24 h, 37° C. | — | |
| 8 | 0 h, 37° C. | unreduced | 10.4 |
| 9 | 4 h, 37° C. | — | 4.0 |
| 10 | 24 h, 37° C. | — | <0.5 |
| 11 | 24 h, 22° C. | unreduced | 8.3 |
| 12 | 4 h, 22° C. | — | 8.6 |
| 13 | 0 h, 22° C. | — | 10.6 |
| 14 | 24 h, 22° C. | reduced | |
| 15 | 4 h, 22° C. | — | |
| 16 | 0 h, 22° C. | — | |
| 19 | MW markers | | |

Plasma derived FVIII-HC (300 U/ml) was diluted 4 fold in 0.05% BSA, 50 mM tris, 0.1M Nacl, 0.02% $NaN_3$, 150 µM 2-ME, pH 7.4 and incubated at 22° C. and 37° C. At t=0, 4, 24 h samples were freezed at −80° C. The samples were thawn and analysed (unboiled) reduced and unreduced in Western blot. Furthermore, the samples were diluted 300 fold and tested for combination with FVIII-LC (WO 88/00210).

The invention is further explained with reference to the drawings in which FIG. 1 shows Western blot of FVIII-HC incubated at 22° C. and 37° C. (samples are the same as in Table 1).

Description of plasmids
Plasmid—Description pPR49—cDNA encoding a Factor VIII variant, in which 880 amino acids are deleted in the B-region (the variant is identical to the one encoded by the pLA-2 plasmid in PCT Patent Application, Publication No. WO 86/06101), has been inserted into the expression vector pSV7d (Truett et al., 1985, DNA 4; 333–349).

pPR60—cDNA encoding a Factor VIII variant, in which Arg-740 has been fused directly to Ser-1690, has been inserted into pSV7d.

pSVF8-92E—cDNA encoding the Factor VIII derived 92 kD peptide (heavy chain) has been inserted into pSV7d.

pSVF8-80K—cDNA encoding the Factor VIII derived 80 kD peptide (light chain) has been inserted into pSV7d.

EXAMPLE 1

The Effect of Growth Temperature on the Yield of Proteins with Factor VIII Activity The expression plasmids pPR49 and pPR60 were transfected to COS-7 monkey cells (Gluzman, 1981, Cell 23; 175–182) by usage of the calcium phosphate technique (Graham and van der Eb, 1973, Virology 52; 456–467) with the modifications described in: DNA Cloning, a Practical Approach, Vol. I+II/IRL Press. (Each plasmid was totally transfected to eight 5 cm's dishes: 2 times 2 dishes determined for expression at 37° C. and 27° C., respectively, in a serum containing medium (10%), and the same number of dishes in serum free medium). 16 hours post transfection the media were changed; half the dishes were shifted to serum free medium. 40 hours post transfection the media were changed and half the dishes were transferred to a 27° C. incubator. After additional 24 hours the media were harvested and the Factor VIII activity was determined by usage of the Kabi coatest chromogenic assay method. The results are listed in Table 2:

TABLE 2

| Plasmid | Temp. (°C.) | Chromogenic activity (mU/ml/day) + serum | − serum |
|---|---|---|---|
| pPR49 | 37 | 1023 | 277 |
| " | 37 | 1028 | 248 |
| " | 27 | 1862 | 1051 |
| " | 27 | 1695 | 977 |
| pPR60 | 37 | 89 | >138 |
| " | 37 | 104 | >138 |
| " | 27 | 336 | 387 |
| " | 27 | 322 | 401 |

EXAMPLE 2

The Combined Effect of Low Growth Temperature and Short Medium Residence Time on the Yield of Factor VIII Heavy Chain from a CHO Cell Line The CHO (Chinese Hamster Ovary) cell line DUKX-B11 Urlaub and Chasin, 1980, PNAS 77; 4216–4220), which is mutated in the dihydrofolate reductase gene, was co-transfected with the plasmids pSVF8-92E and pSVF8-80K plus a plasmid encoding the dihydrofolate reductase. (These co-transfections are described in U.S. patent application Ser. No. 82,989).

Hereby a clone (10C2D2) was isolated, characterized by producing 10 fold more heavy chain (HC) than light chain (LC) when it is grown at 37° C. When 10C2D2 is grown at 27° C. the yield of HC is raised dramatically seen in relation to the yield of LC (see Table 3).

TABLE 3

| Temp. (°C.) | Culturing time (hours) | Vol. med./T-80 flask (ml) | HC:Ag* (U/ml) | LC:Ag* (U/ml) |
|---|---|---|---|---|
| 37 | 24 | 10 | 3.2 | 0.36 |
| 27 | 24 | 10 | 18.4 | 0.28 |

*HC:Ag and LC:Ag were measured in specific immuno assays (Nordfang et al., 1988, Br. J. Haematol. 68; 307–312; Nordfang et al., 1985, Thromb. Haemostas. 53: 346–350).

By shortening the medium residence time to only 2 hours a greater yield of HC per day is achieved (Table 4):

TABLE 4

| Temp. (°C.) | Culturing time (hours) | Vol. med./T-80 flask (ml) | HC:Ag (U/ml) | HC:Ag (U/ml/day) |
|---|---|---|---|---|
| 37 | 24 | 10 | 3.2 | 3.2 |
| 27 | 24 | 10 | 18.4 | 18.4 |
| 27 | 2 | 10 | 7.5 | 90 |
| 27 | 2 | 3 | 24.0 | 288 |

EXAMPLE 3

Production of FVIII:HC in Opticell Bioreactor at 28°–30° C. by 10C2D2

In the Opticell bioreactor the cells are cultured on a ceramic matrix, the Opticore, and the culture media is circulated through the Opticore. The oxygen content, pH, medium feed and harvest are all measured and controlled by the system.

The average medium circulation time was 5 hours (150 ml per hour with a volume in the reservoir+Opticore of 750 ml). The harvest was collected at 5° C. and frozen every 24 h at −80° C.

The cells were cultured at 37° C. until near confluent (measured by the oxygen comsumption rate) and the temperature was lowered to 28°–30° C. for production of FVIII:HC.

The cells were kept at the production temperature for 1000 hours. The oxygen comsumption rate decreased in a couple of hours when the temperature was lowered from 37° C. to 30° C. and from 30° C. to 28° C., but each time the oxygen comsumption rate gradually increased again. Thus the cells could be maintained at the lower temperature even for longer than the 1000 hours.

In Table 5 the medium composition and feed/harvest volumes as well as the FVIII:HC levels for some of the harvest samples are shown.

TABLE 5

| Hours after temperature shift to 28–30° C. | Medium DMEH + 1% ITS | Feed/ Harvest ml/h | FVIII:HC U/ml | FVIII:HC U/day |
|---|---|---|---|---|
| 408 | + 2% FCS | 100 | 15.1 | 36240 |
| 432 | + 2% FCS | 150 | 10.9 | 39240 |
| 456 | + 2% NCS | 150 | 11.0 | 39600 |

EXAMPLE 4

The Effect of Low Growth Temperature on Yield of Factor VIII Light Chain from COS-7 Monkey Cells An expression plasmid designated pPR77 encoding Factor VIII light chain was transfected to COS-7 cells in the same manner as described in Example 1. The plasmid was transfected to four 5 cm dishes: two times two dishes determined for expression at 37° C. and 27° C., respectively. The media (DMEM+10% FCS) were changed 16 and 40 hours post transfection (at 40 hours half the dishes were transferred to a 27° C. incubator). After additional 24 hours the media were harvested. The content of Factor VIII light chain was determined as described in Example 2. The results are given in Table 6.

TABLE 6

| Temp. (°C.) | LC:Ag (U/ml/day) |
|---|---|
| 37 | 0.33 |
| 37 | 0.30 |
| 27 | 1.25 |
| 27 | 0.85 |

EXAMPLE 5

The Effect of Low Growth Temperature on the Yield of Protein-Complex with Factor VIII Activity from CHO Cells Transfected with Plasmids Encoding Each of the Two Subunits of Factor VIII: the Heavy Chain and the Light Chain The DHFR(−) CHO cell line DG44 (cf. G. Urlaub et al., Proc. Natl. Sci., USA 77; 4216–4220, 1980) was first transfected with a plasmid encoding the light chain of Factor VIII and the DHFR gene. By selection of DHFR(+) cells a stable light-chain producer was isolated. This new cell line was co-transfected with a plasmid encoding the heavy chain of Factor VIII (and the DHFR gene) and a plasmid encoding the neo gene (pSV2neo; P. J. Southern and P. Berg, Journal of Molecular and Applied Genetics 1; 327–341, 1982). Transfectants were isolated in medium containing 700 µg Geneticin (G418 Sulphate, Gibco) per ml. Cells from the primary pool were propagated directly into medium containing 0.1 µM MTX. Cells isolated in this way were seeded into two T-80 flasks, called A and B. At confluence the media (DMEM+10% DFCS+700 µg Geneticin/ml+0.1 µM MTX) were changed (10 ml) and the flasks were incubated 24 hours at 37° C. whereafter media samples were collected. The media were renewed and the B flask was transferred to a 27° C. incubator. Again the flasks were incubated for 24 hours followed by collection of media samples and renewing of media. This procedure was repeated for another two days (the A flask still at 37° C. and the B flask still at 27° C.). The Factor VIII activity was determined by the Kabi coatest chromogenic assay method. The results are given in Table 7.

TABLE 7

| Day | Temp. (°C.) | Chromogenic activity (U/ml/day) |
| --- | --- | --- |
| Flask A: | | |
| 1 | 37 | 0.42 |
| 2 | 37 | 0.77 |
| 3 | 37 | 0.84 |
| 4 | 37 | 1.0 |
| Flask B: | | |
| 1 | 37 | 0.50 |
| 2 | 27 | 1.20 |
| 3 | 27 | 1.72 |
| 4 | 27 | 3.2 |

I claim:

1. A method for obtaining a Factor VIII heavy chain and Factor VIII light chain protein-complex having Factor VIII activity comprising (a) expressing the Factor VIII heavy chain, the Factor VIII light chain and a selectable marker from two expression cassettes wherein the first expression cassette comprises a DNA sequence encoding a Factor VIII heavy chain and the second expression cassette comprises a DNA sequence encoding a Factor VIII light chain and wherein a DNA sequence encoding a selectable marker is expressed from either or both expression cassettes, in an in vitro culture of a mammalian cell in which said mammalian cell is cultured at a;

(b) selecting for the expression of the Factor VIII heavy chain and Factor VIII light chain, and (c) isolating the Factor VIII heavy chain and Factor VIII light chain complex.

2. The method according to claim 1 in which the mammalian cell is a COS cell, CHO cell or BHK cell.

3. A method for obtaining a Factor VIII heavy chain and a Factor VIII light chain protein complex with Factor VIII activity comprising the following steps:

(a) introducing into a mammalian cell a plasmid comprising a DNA sequence encoding a Factor VIII heavy chain and a plasmid comprising a DNA sequence encoding a Factor VIII light chain and a plasmid comprising a DNA sequence encoding a selectable marker;

(b) culturing the mammalian cell at 25° C. to 30° C.; and (c) isolating said protein complex.

* * * * *

UNITED STATES PATENT AND TRADEMARK OFFICE
CERTIFICATE OF CORRECTION

PATENT NO.   : 5,610,033
DATED        : March 11, 1997
INVENTOR(S)  : Rasmussen et al.

It is certified that error appears in the above-indentified patent and that said Letters Patent is hereby corrected as shown below:

Col. 6, line 17:    replace "mammalian cell is cultured at a;"

with - - mammalian cell is cultured at a temperature from 25C to 30C; - -.

Signed and Sealed this

Twenty-second Day of July, 1997

Attest:

BRUCE LEHMAN

Attesting Officer

Commissioner of Patents and Trademarks